United States Patent [19]

Bell et al.

[11] Patent Number: 4,662,883
[45] Date of Patent: May 5, 1987

[54] SELF-SEALING VALVE FOR FLUID FILLABLE DEVICE

[75] Inventors: Julie D. Bell; Ray H. Dormandy, Jr., both of Santa Barbara, Calif.

[73] Assignee: Mentor Corporation, Minneapolis, Minn.

[21] Appl. No.: 756,408

[22] Filed: Jul. 17, 1985

[51] Int. Cl.[4] .......................... A61F 2/12; A61F 2/02; F16K 15/20
[52] U.S. Cl. ........................................... 623/8; 623/11; 137/223; 138/89; 138/128
[58] Field of Search ................. 137/223; 623/7, 8, 11; 138/89, 109, 119, 128; 174/DIG. 8

[56] References Cited

U.S. PATENT DOCUMENTS

| 564,502 | 7/1896 | Brookes | 137/223 |
|---|---|---|---|
| 1,008,641 | 11/1911 | Gregory | 137/223 |
| 1,551,099 | 8/1925 | Goldsmith et al. | 273/65 C |
| 2,142,414 | 1/1939 | Riddell | 273/65 |
| 2,516,129 | 7/1950 | Leo et al. | 2/42 |
| 2,568,976 | 9/1951 | Andrews | 251/119 |
| 2,697,229 | 12/1954 | Krueger | 2/267 |
| 2,700,980 | 2/1955 | Andrews | 137/223 |
| 2,795,425 | 6/1957 | Orms | 273/58 |
| 2,933,120 | 4/1960 | Siedow | 152/429 |
| 3,204,959 | 9/1965 | Nicholls | 273/58 |
| 3,410,300 | 12/1968 | Mondano | 137/223 |
| 3,523,563 | 8/1970 | Mirando | 141/313 |
| 3,565,078 | 2/1971 | Valliancourt | 128/349 |
| 3,584,671 | 6/1971 | Kampa | 152/429 |
| 3,600,718 | 8/1971 | Boone | 3/36 |
| 3,852,832 | 12/1974 | McGhan et al. | 3/36 |
| 3,852,833 | 12/1974 | Köneke et al. | 3/36 |
| 3,883,902 | 5/1975 | Lynch | 3/36 |
| 3,939,875 | 2/1976 | Osborn et al. | 138/119 |
| 4,178,643 | 12/1979 | Cox, Jr. | 3/36 |
| 4,263,682 | 4/1981 | Bejarano | 3/36 |
| 4,459,318 | 7/1984 | Hyans | 427/36 |

FOREIGN PATENT DOCUMENTS 9698 of 1902 United Kingdom ............... 137/223

Primary Examiner—Martin P. Schwadron
Assistant Examiner—Sheri M. Novack
Attorney, Agent, or Firm—Kinney & Lange

[57] ABSTRACT

An improved self-sealing valve for use in a fluid fillable device includes a main body portion and a channel within the main body portion for receiving a fill tube. The improvement includes a sealing portion with the channel extending therethrough and movable from a fluid flowable position with the fill tube inserted in the channel to a curled, fluid sealing position when the fill tube is removed from the channel.

6 Claims, 7 Drawing Figures

SELF-SEALING VALVE FOR FLUID FILLABLE DEVICE

BACKGROUND OF THE INVENTION

1. Field of the Invention

The present invention relates to self-sealing valves, and in particular, it relates to self-sealing valves for use with fill tubes.

2. Description of the Prior Art

In recent developments in inflatable prosthetic devices, it has been found desirable to progressively inflate the prosthetic device over a period of time. This has required the use of subcutaneous injection sites connected to the inflatable prosthetic device by a fill tube. The fill tube is typically inserted into the inflation chamber of the device through a valve. The valve is typically made of two sheets of silicone rubber bonded together along their edges with a channel therebetween. If a fill tube is disposed within the valve for a long time, stresses in the silicone rubber forming the channel result in the valve not sealing adequately once the fill tube is removed. The channel becomes somewhat "set" in an open position and remains in the set position once the fill tube has been removed.

A number of patents directed to prosthetic inflatable devices show valves which are constructed of two sheets of silicone elastomer bonded together along two edges to form a channel. None of the valves illustrated in the immediately below-listed patents are constructed to avoid the channel being permanently deformed due to the stress caused on the material by the fill tube inserted into the channel over a long period of time:

| Inventor | U.S. Pat. No. |
| --- | --- |
| Hyans | 4,459,318 |
| Bejarano | 4,263,682 |
| Cox, Jr. | 4,178,643 |
| Köneke et al | 3,852,833 |
| McGhan et al | 3,852,832 |
| Valliancourt et al | 3,565,078 |
| Krueger | 2,697,229 |

The Lynch U.S. Pat. No. 3,883,902 and the Boone U.S. Pat. No. 3,600,718 show other types of valves used in inflatable prosthetic devices. The valve illustrated in the Lynch Patent shows a complicated sealing arrangement and the valve shown in the Boone Patent shows a valve using a silicone gel chamber as a sealing arrangement.

Still other patents show inflatable devices other than prosthetic devices using a variety of valving arrangements for the introduction of air. However, similar to the patents directed to prosthetic devices, the valves shown in the immediately below-listed patents are also not designed for the retention of a fill tube for a long period of time.

| Inventor | U.S. Pat. No. |
| --- | --- |
| Kampa | 3,584,671 |
| Mirando | 3,523,563 |
| Mondano | 3,410,300 |
| Nicholls | 3,204,959 |
| Siedow | 2,933,120 |
| Orms | 2,795,425 |
| Andrews | 2,568,976 |

| Inventor | U.S. Pat. No. |
| --- | --- |
| Goldsmith et al | 1,551,099 |

SUMMARY OF THE INVENTION

The present invention is directed to an improved valve for use in a fluid fillable device. The valve includes a main body and a channel within the main body portion for receiving a fill tube. The improvement comprises a sealing portion with the channel extending therethrough and movable from a fluid flowable position with the fill tube inserted in the second channel, to a curled, fluid sealing position when the fill tube is removed from the second channel.

In a preferred embodiment, the valve is made of two sheets of silicone rubber that includes both the main body and the sealing portion. The two layers are bonded to each other by vulcanization with a removable Teflon strip retained between the two sheets during vulcanization to form the fluid channel. The sealing portion is stretched, placing it in tension and a strip of unstretched silicone rubber is vulcanized to the sealing portion. The attachment of the unstretched silicone strip to the sealing portion causes the sealing portion to curl. The sealing portion uncurls when the filling tube is inserted into the channel and curls when the filling tube is removed to provide a positive seal to the channel.

DETAILED DESCRIPTION OF THE PREFERRED EMBODIMENTS

Figure 1:
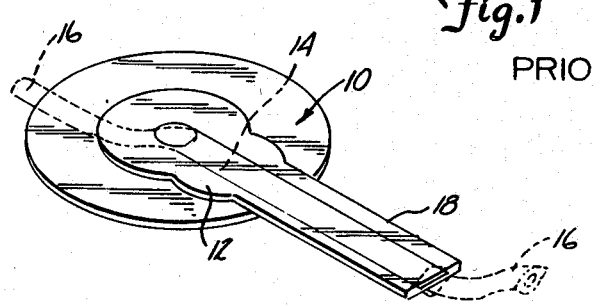
FIG. 1 is a perspective view of a prior art valve.

FIG. 1 illustrates a prior art valve 10 manufactured and marketed by the assignee of the present application for use in fluid fillable prosthetic devices, such as mammary prostheses. The valve includes a main body 12 having a channel 14 through which a fill tube 16 is inserted. The valve also includes a portion 18 that extends into the inflation chamber of the prosthesis and which acts as a seal when the fill tube is removed from the valve. The valve is constructed by vulcanizing two sheets of silicone rubber to form both the main body and the portion extending into the inflation chamber. The channel between the two pieces of vulcanized silicone rubber is formed by placing a removable Teflon ribbon between the two sheets during vulcanizing. The valve channel is typically filled with silicone gel as an aid in preventing leakage through the channel once the fill tube is removed. The gel has been found to be somewhat effective in blocking the channel. Pressure within the inflation chamber of the prosthesis, once the prosthesis has been filled, also acts on the two sheets of silicone forming the valve to help in sealing the valve.

The prior art valve 10 has been somewhat effective in inflatable prosthetic devices when the fill tube has been left in the channel 14 for only a short period of time, such as less than one hour. It has been found that if the fill tube was left in the valve for more than one hour, the silicone rubber sheeting forming the channel had become stressed resulting in the channel being set open and leakage resulting.

Figure 2:
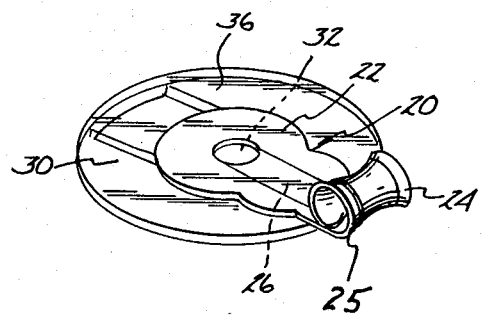
FIG. 2 is a perspective view of the valve of the present invention with the sealing portion in a curled state.
Figure 3:
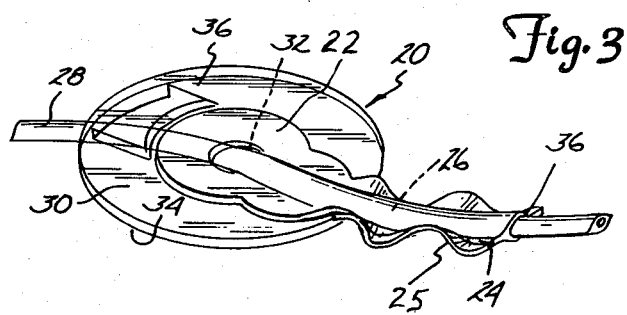
FIG. 3 is a perspective view of the valve of the present invention with the sealing portion uncurled and the valve containing a filling tube.

Referring to FIGS. 2 and 3, the valve of the present invention is generally indicated at 20. The valve includes a main body portion 22 and a sealing portion 24. The sealing portion 24 is illustrated in FIG. 2 in a curled state and the sealing portion 24 is illustrated in FIG. 3 in an uncurled state, or fluid fillable position.

The valve 20 is made of a medical grade silicone polymer. The main body portion 22 and sealing portion 24 are formed of two sheets of silicone polymer vulcanized together. A channel 26 for receiving a filling tube 28 is formed between the two layers of silicone sheeting by inserting a removable strip of Teflon before the two layers of silicone sheeting are vulcanized. The sealing portion is stretched and a strip 25 of unstretched silicone rubber is bonded to the sealing portion to make the portion 24 curl.

Figure 4:
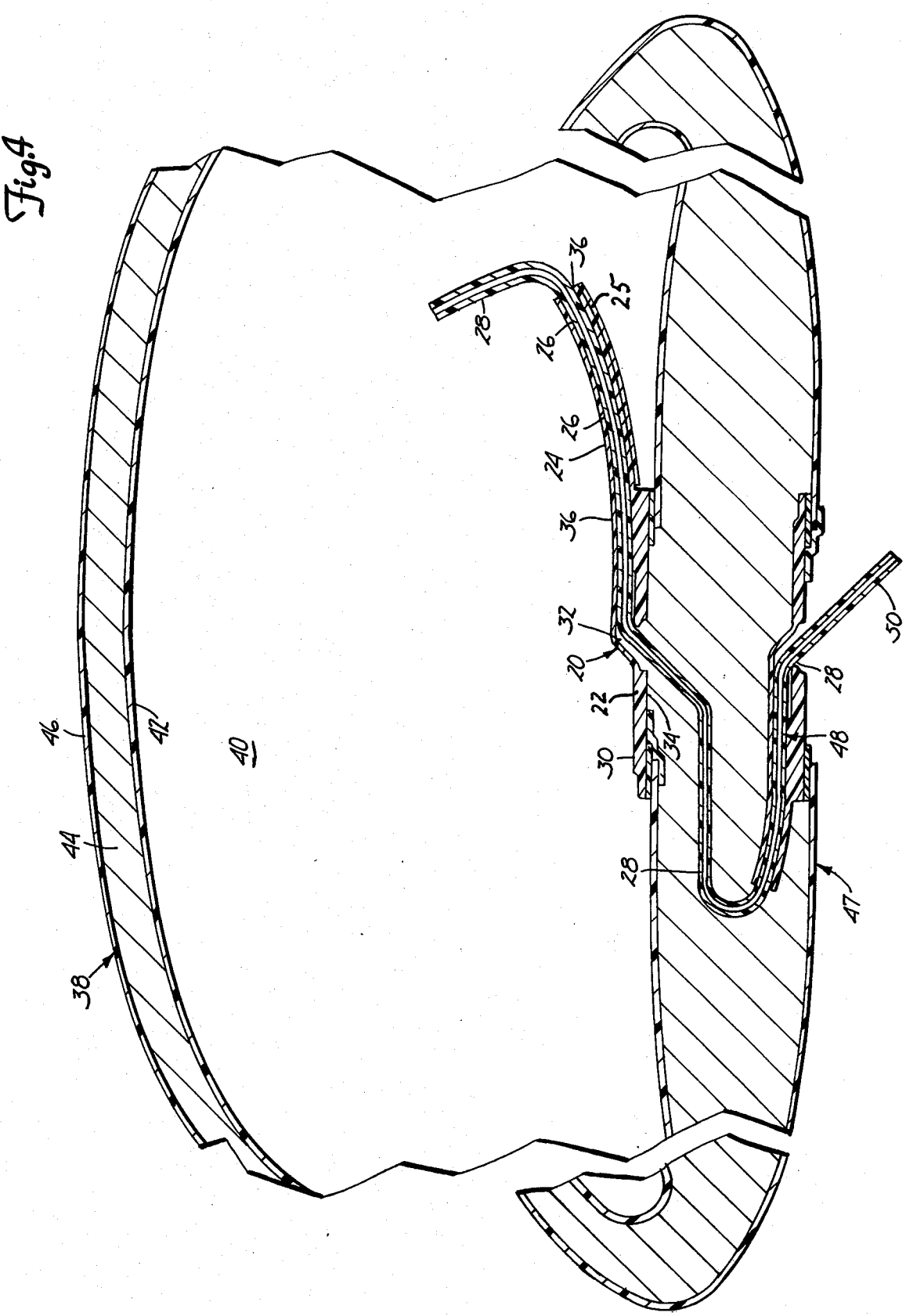
FIG. 4 is a sectional view of a mammary prosthesis using the valve of the present invention with portions broken away.

The main body portion 22 is fixedly attached, such as by vulcanization or adhesive bonding, to a sheet 30 of silicone polymer that is in turn used to attach the valve to a prosthetic device such as a mammary prosthesis illustrated in FIG. 4. The main body of the valve 22 has an opening 32 that faces a side 34 that is disposed toward the outside of an inflation chamber. A side 36 of the valve faces an interior of the inflation chamber.

The channel 26 has an interior opening 36 that is disposed at the end of the sealing portion 26 and in the interior of the inflation chamber. The filling tube 28 extends through the opening 32, through the channel 26 and out the opening 36.

Referring to FIG. 4, in which a sectional view of a double-chambered mammary prosthesis generally indicated at 38 is illustrated, the valve 20 of the present invention is shown with the fill tube 28 within the channel and attached to an inner chamber 40 of the prosthesis 38. The double-chambered mammary prosthesis 38, sometimes known as a double lumen prosthesis, includes inner inflatable chamber 40 defined by an expandable envelope 42 that is encased in a fluid 44 contained by an outer envelope 46. The fluid 44 is preferably made of a medical grade silicone gel that is well known in the art. Although the mammary prosthesis shown is a specific example, the valve of the present invention is useful for other prosthetic devices and for other inflatable devices, which are includable within the scope of the present invention.

In the double lumen mammary prosthesis 38, the fill tube 28 extends through two valves, the second valve indicated by reference character 48 and located on a back side 47 of the exterior wall 46 is preferably the valve of the present invention, although the valve 48 could also be the prior art valve 10. An exterior end portion 50 of the tube 28 extends out of the valve 48 and is connected to a suitable injection site (not shown) such as a subcutaneous injection site disclosed and illustrated in the Radovan et al U.S. Pat. No. 4,217,889 and the Schulte U.S. Pat. No. 4,190,040 which are herein incorporated by reference. The subcutaneous injection site (not shown) permits implantation of the mammary prosthesis and the progressive inflation of the mammary prosthesis after implantation by injection of a saline solution using a hypodermic needle (not shown).

Figure 5:
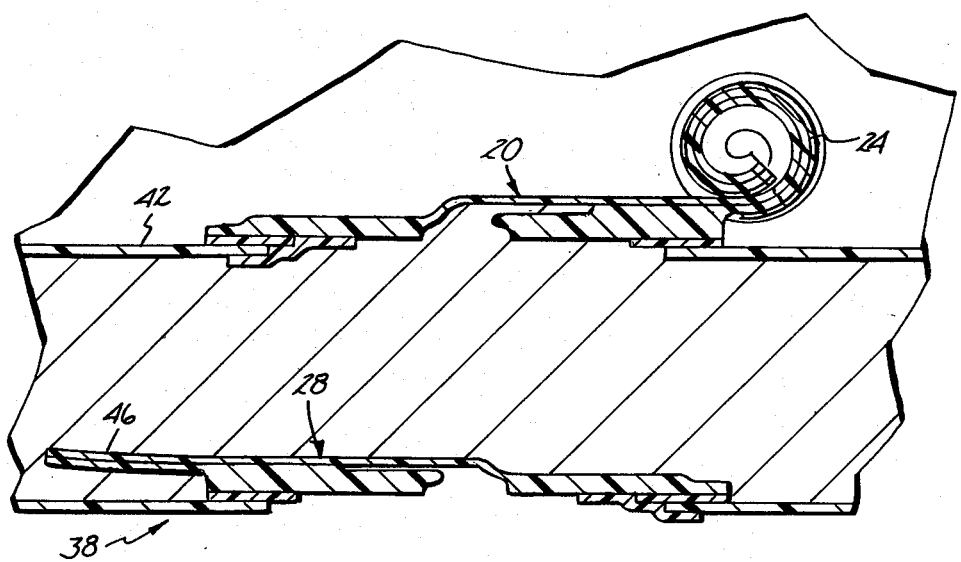
FIG. 5 is a sectional view of the valve of the present invention and the prosthesis of FIG. 4 in a curled position with additional portions of the prosthesis broken away.

As best seen in FIG. 4, the valve 20 provides a unique mechanism for introducing the fill tube through the outer envelope 46 and gel 44 into the inner chamber 40 for the introduction of a different inflation fluid, such as saline. In FIG. 5, the valves 20 and 48 are shown as part of the double lumen mammary with the fill tube 28 withdrawn. A lubricant, such as silicone gel or a fluorocarbon, is provided in the channel of the valve to help in the withdrawal of the fill tube. The fill tube is withdrawn when the mammary is inflated to the desired size and when the subcutaneous injection site is removed from the patient, a procedure which is well known. When the fill tube is withdrawn, the sealing portion 24 curls along the longitudinal axis of the channel 26 providing a positive seal. Any stressed portions of the channel that have been set in an open position are closed due to the curling action of the portion 24. The sealing portion does not require positive pressure within the inflation chamber to provide a seal or gel inserted within the channel to effect closure. The forces provided in the sealing portion provide the positive closure forces.

Figure 6:
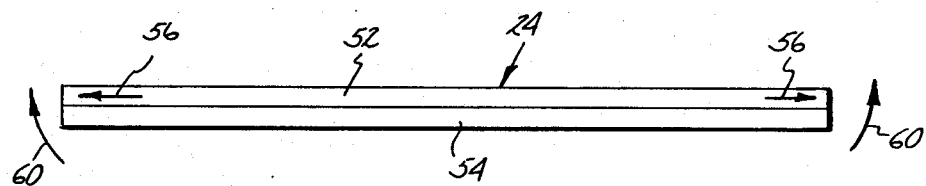
FIGS. 6 and 7 are diagrammatical views showing what is believed to be the mechanism and forces causing the positive closure of the channel in the sealing portion.
Figure 7:
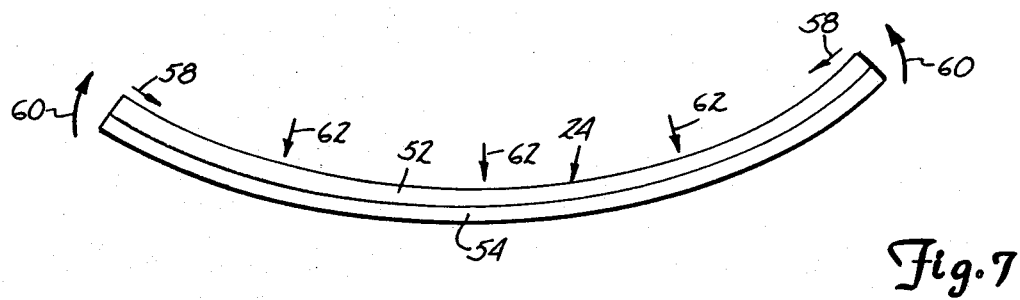

FIGS. 6 and 7 provide a further explanation of what is believe to be the mechanism that provides for the positive closure of the sealing portion 24. The sealing portion 24 includes a stressed layer 52 and an unstressed layer 54. The stressed layer 52 is stressed by placing it in tension as indicated by arrows 56 prior to vulcanization to the unstressed layer 54. Due to the elasticity of silicone rubber, the stressed layer 52 then provides compressive forces in the general direction of arrows 58, as illustrated in FIG. 7, in both layers 52 and 54 since the layers are now bonded to each other. The entire sealing portion 24 then curls in the direction of arrows 60. Further forces are provided, due to the curling action in the general direction of arrows 62 providing a positive force to close the channel 26 and overcome any portions of the channel 26 that are set open due to the long-term occupancy of the fill tube within the channel.

Although the present invention has been described with reference to preferred embodiments, workers skilled in the art will recognize that changes may be made in form and detail without departing from the spirit and scope of the invention.

What is claimed is:

1. An improved valve for use in a fluid fillable device, the valve including a main body portion and a longitudinal channel for receiving a fill tube extending through the main body portion, the improvement comprising:
   a longitudinal sealing portion having a longitudinal axis with the channel extending through the sealing portion along the axis, the sealing portion movable from a fluid flowable position with the fill tube inserted in the channel to a curled, fluid sealing position when the fill tube is removed from the channel wherein the sealing portion includes a first layer of stretched silicone elastomer with the first layer stretched along the longitudinal axis and a second layer of unstretched flexible material bonded to the first layer.

2. An improved valve for filling and sealing an inflatable prosthetic device, a fill tube being insertable through a longitudinal channel in the valve having a longitudinal axis, the improvement comprising:

first and second longitudinal layers of flexible material defining the channel and a third layer of an elastic material being bonded to the second layer of material in a stretched state causing the first and second layers to curl along the longitudinal axis of the channel when the fill tube is not within the channel.

3. An implantable device comprising:
outer shell means;
inner shell means disposed within the outer shell means for filling with a first inflatable fluid;
a second fluid being disposed between the inner and outer shells;
first valve means positioned on the outer shell for sealing the outer shell means and having channel means adaptable for receiving a fill tube; and
second valve means positioned on the inner shell means for sealing the inner shell means and a longitudinal sealing portion having a longitudinal channel for receiving the fill tube, the longitudinal sealing portion having a longitudinal axis with the channel extending through the sealing portion along the axis, the sealing portion being movable from a fluid flowable position when the fill tube is inserted in the channel to a curled, fluid-sealing position when the fill tube is removed from the channel wherein the sealing portion includes a first layer of stretched silicone elastomer with the first layer stretched along the longitudinal axis and a second layer of unstretched flexible material bonded to the first layer; and
wherein the first and second valve means are positioned such that the fill tube extends through the channel means of the first valve means and through the channel of the second valve means.

4. An implantable device comprising:
outer shell means;
inner shell means disposed within the outer shell means for filling with a first inflatable fluid;
a second fluid being disposed between the inner and outer shells;
first valve means positioned on the outer shell for sealing the outer shell and having channel means adaptable for receiving a fill tube;

second valve means positioned on the inner shell means for sealing the inner shell means, the second valve means including a longitudinal channel having a longitudinal axis for receiving the fill tube, the second valve means having a sealing portion with first and second longitudinal layers of flexible material defining the channel and a third layer of an elastic material being bonded to the second layer of material in a stretched state causing the first and second layers to curl along the longitudinal axis of the channel when the fill tube is not within the channel; and
wherein the first and second valve means are positioned such that the fill tube extends through the channel means of the first valve means and through the channel of the second valve means.

5. An implantable device comprising:
an expandable envelope defining a fluid fillable chamber; and
valve means for providing access to the chamber and for sealing the chamber and including a body portion having a longitudinal sealing portion with a longitudinal channel along a longitudinal axis with the channel extending through the sealing portion along the axis, the sealing portion movable from a fluid flowable position with a fill tube inserted in the channel to a curled, fluid sealing position when the fill tube is removed from the channel wherein the sealing portion includes a first layer of stretched silicone elastomer with the first layer stretched along the longitudinal axis and a second layer of unstretched flexible material bonded to the first layer.

6. An implantable device comprising:
an expandable envelope defining a fluid fillable chamber; and
valve means for providing access to the chamber and for sealing the chamber and including a body portion having a longitudinal channel disposed along a longitudinal axis and first and second longitudinal flexible layers defining the channel and a third layer of an elastic material being bonded to one of the flexible layers in a stretched state causing the first and second layers to curl along the longitudinal axis of the channel.

* * * * *